United States Patent [19]

Blake-Coleman et al.

[11] Patent Number: 4,796,468

[45] Date of Patent: Jan. 10, 1989

[54] APPARATUS FOR MEASURING FLUID DENSITY

[75] Inventors: Barry Blake-Coleman; David Clarke, both of Salisbury, United Kingdom

[73] Assignee: Public Health Laboratory Service Board, England

[21] Appl. No.: 22,213

[22] Filed: Mar. 5, 1987

Related U.S. Application Data

[63] Continuation-in-part of Ser. No. 832,713, Jan. 31, 1986, abandoned.

[30] Foreign Application Priority Data

Apr. 3, 1984 [GB] United Kingdom ............ 8408527

[51] Int. Cl.$^4$ .............................................. G01N 9/00
[52] U.S. Cl. ................................................. 73/32 A
[58] Field of Search ............... 73/32 A, 580; 435/291; 331/65

[56] References Cited

U.S. PATENT DOCUMENTS 4,655,075 4/1987 Albert et al. .................. 73/32 A

FOREIGN PATENT DOCUMENTS 711432 1/1980 U.S.S.R. .
1062562 12/1983 U.S.S.R. ........................ 73/32 A

OTHER PUBLICATIONS

V. J. Matveev et al., "Cryogenic Vibration Densitometer", *Measurement Techniques*, vol. 26, No. 8, Aug. 1983, pp. 664–667.

Primary Examiner—Stewart J. Levy
Assistant Examiner—Robert P. Bell
Attorney, Agent, or Firm—Lowe, Price, LeBlanc, Becker & Shur

[57] ABSTRACT

Apparatus for use in measuring fluid density comprises a fluid carrying helical sample tube 50 made of a conductive material for passing current therethrough. A cylindrical coil fixing sleeve 58 form surrounds the helical sample tube and engages the tube to prevent relative movement of the turns. A high flux permanent magnet 60 is carried on one post 54 and is aligned along the axis of the tube. The magnetic field established by magnet 60 and the pole extension 64 will subject each current-carrying length element of the sample tube to an axial force, the sum of these forces resulting in a bodily axial movement of the sample tube. The sample tube is excited to spring resonance by passing current through the sample tube. The resonant frequency is measured and is indicative of the mass of the fluid contained in the coil and thereby of the fluid density.

18 Claims, 7 Drawing Sheets

APPARATUS FOR MEASURING FLUID DENSITY

This application is a continuation-in-part of application Ser. No. 832,713 filed 1-31-86 now abandoned.

BACKGROUND OF THE INVENTION

This invention relates to the measurement of the density of fluids.

There is an established technique known as vibration densitrometry which involves—in one form—filling a resiliently supported vessel with sample fluid and electromechanically exciting the vessel to a vibrational resonance. The resonant frequency can be determined precisely and is indicative of the mass contained in the known volume of the vessel and thereby of the fluid density. Reference is directed, by way of example, to U.S. Pat. No. 3,523,446.

Various shapes of vessel have been put forward as advantageous, including a sphere, a cylinder and a U-tube. If the apparatus is to have the sensitivity necessary to detect very slight changes in fluid density, a significant body of fluid must be contained within the vessel. However, with a sphere or cylinder of relatively large dimensions, the difficulty is encountered that the time of travel of a pressure wave through the contained fluid approaches the period of vibrational movement of the vessel. Under those circumstances it is no longer accurate to treat the vessel and fluid as together defining a rigid body moving in simple harmonic motion. Effectively, the central volume of the fluid plays less than its expected part in damping the motion of the vessel so that an erroneous density value is produced. This error becomes more significant with fluids of higher viscosity.

A further difficulty that is particularly acute with, for example, a vessel in the shape of a U-tube, is that with increasing dimensions the deviations from simple harmonic motion become more marked leading again to erroneous density values. In addition, there is an evident disadvantage in increasing the overall size of the measurement apparatus, particularly if it is the intention to mount the apparatus within process plant to provide on-line monitoring of density.

It has been proposed to deal with these problems by employing as the vessel an elongate tube shaped as a helical spring. Reference is directed, for example, to USSR Inventor's Certificate No. 711432 and USSR Patent No. 1062562. In each case the disclosed apparatus takes the form of a helical sample tube fixed at its ends and carrying at the mid length a pole piece driven by an electromagnet. Torsional waves are set up in the helical tube at a resonant frequency which is influenced by both the density and viscosity of the sample fluid contained within the tube. The resonant frequency is measured in a suitable manner.

There is a difficulty with this apparatus that the measurement it produces is both density and viscosity dependent. If viscosity remains constant, a separate measurement will enable a value to be determined for density, but this is troublesome and can slow down the procedure to a point where on-line determination becomes impractical. If the viscosity is not constant, the usefulness of the apparatus is in real doubt.

It is an object of this invention to provide improved apparatus for use in the measurement of fluid density which goes some way to overcoming the above disadvantages.

SUMMARY OF THE INVENTION

According to one aspect of this invention there is provided apparatus for use in measuring fluid density comprising a rigid base structure; a helical sample tube having a tube wall which is electrically conductive at least in a continuous portion thereof extending throughout a substantial length of the sample tube, the sample tube being fixed at its ends on said base structure; sample feed means for introducing into said sample tube a body of fluid whose density is to be measured; drive means for the sample tube, comprising current means for passing an electrical current along said length of the sample tube and reactor means mounted on the base structure and adapted through magnetic coupling with the current carrying sample tube to excite bodily vibrational movement of the sample tube along the helical axis thereof; and monitoring means for monitoring said vibrational movement to determine the fluid density.

In another aspect, the present invention consists in apparatus for use in measuring fluid density, comprising a thin elongate tube fixed only at its ends and folded between said ends to provide a vibratory spring system; a pair of electro-mechanical drive means operating on the tube at spaced locations adjacent respective opposite ends of the tube, said electro-mechanical drive means being supplied with out of phase electrical signals to excite bodily vibrational movement of the tube and monitoring means including a transducer operating near the mid-length of the tube for monitoring the vibratory movement of the tube to determine fluid density.

DESCRIPTION OF THE PREFERRED EMBODIMENTS

Figure 2:
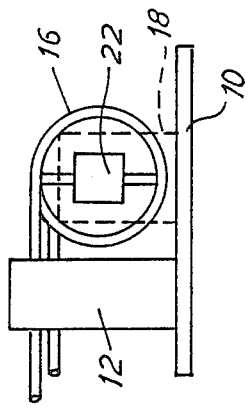
FIG. 2 is an end view of the apparatus shown in FIG. 1.
Figure 1:
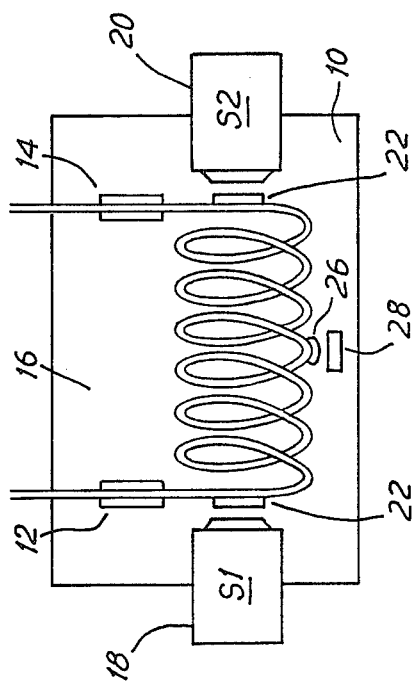
FIG. 1 is a plan view in somewhat diagrammatic form showing apparatus according to one aspect of this invention.

Referring to FIGS. 1 and 2, the apparatus comprises a rigid base plate 10 from which rise two mounting pillars 12 and 14. A coil 16 of thin stainless steel tubing is secured at opposite ends to the pillars 12 and 14; the tube ends passing through the pillars to form fluid inlet and outlet ports. Between the two pillars, the coil has several turns which are freely suspended.

Drive solenoids 10 and 20 are disposed one at each end of the base 10. These solenoids cooperate respectively with ferromagnetic pole pieces 22 and 24 carried on opposite ends of the coil 16. At the coil mid-point, there is provided a position/feedback transducer having fixed and moving portions 28 and 26 respectively. This transducer may take a number of well known forms including capacitive or electromagnetic.

Figure 3:
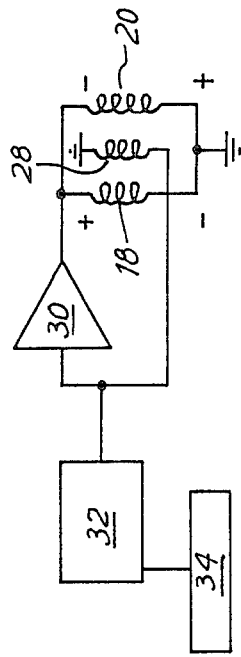
FIG. 3 is a circuit diagram showing the electrical drive for the apparatus shown in FIG. 1.

Referring now to FIG. 3, the transducer coil or other pick up 28 provides an input to amplifier 30, the output of which is connected in antiphase across the two drive solenoids 18 and 20. The amplifier is selected to have a gain which exceeds the losses of the electromechanical system and to have a broad bandwidth.

In operation, sample fluid is passed through the coil either continuously—if the rate at which the sample density changes is small compared with the fluid travel time through the coil—or alternatively in a step-wise manner. Inevitable background vibrations will result in slight movement of the coil which is detected in pick-up 28 with the effect that the movement is amplified through forces applied at opposite ends of the coils through the solenoids. In this way, the electromechanical system is brought to resonance at a frequency which is determined by the natural frequency of the coil and the mass of fluid contained therein. The resonant frequency is measured in frequency meter 32 and passed to a display device 34 which may be calibrated in suitable density units.

The coil 16 has a length which greatly exceeds the tube thickness. In the described example, the length of the tube is 300 mm and the thickness ½ mm giving a length to thickness ratio of 600. Because of the length, a sufficient body of fluid may be accommodated to give reasonable sensitivity. The small thickness of the tube ensures, however, that the time of travel of a pressure wave across the tube is very short compared with the period of vibration so that the entire mass within the tube participates in the vibratory movement. By folding the tube into a helix, the overall dimensions of the apparatus are kept within acceptable limits, notwithstanding the length of the tube.

A form of amplifier which is particularly suited to use with this apparatus will now be described with reference to FIG. 4. The requirements for this amplifier are that the gain and phase shift should be substantially constant for the frequencies of axial mode resonance corresponding with the range of densities likely to be encountered in use, but the frequencies associated with other modes of resonance should be severely attenuated. It is unusally not possible to predict the natural resonant frequency of each mode of resonance and in order to maximise the usable bandwidth of the amplifier without including unwanted resonance modes, it is desirable to have an amplifier the frequency response of which can be tailored in use.

Figure 4:
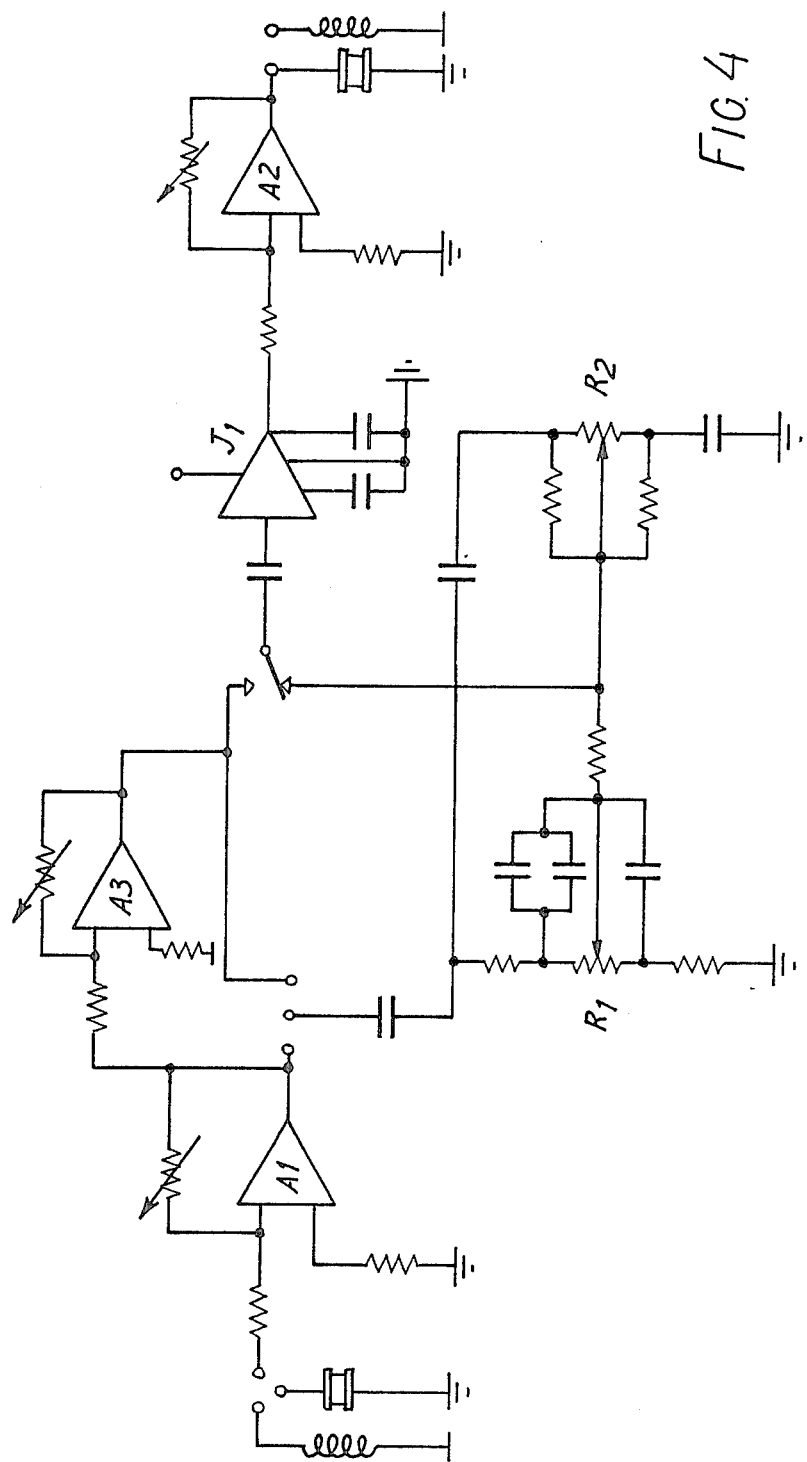
FIG. 4 is a circuit diagram of a preferred amplifier for use in the circuit of FIG. 3.

In the circuit diagram which is FIG. 4, A1 is a variable gain operational amplifier serving as a first stage buffer and impedance matching stage. A further amplification stage comprising operational amplifier A3 may be switched in or not depending on gain requirements, but if no gain is required the gain is set to one to maintain phase relationships. The bandwidth of the amplifier is determined by a filter network including variable logarithmic resistors R1 and R2 which set the limits of the filter pass band. Stage J1 is a control attenuator which functions to limit the system gain. The final stage comprises a further operational amplifier A2 of variable gain.

By the use of this arrangement, an amplifier is provided which has a substantially linear response over a frequency range which can be tailored through control of R1 and R2 to cover the anticipated density range but to avoid unwanted resonance modes.

Because of the ability to accommodate viscous fluids without the errors mentioned above, and because of the capability of producing an output in real time with a continuously flowing sample, the described apparatus is ideal for use in measuring the density of biological matter in fermentation process plants. It is disclosed in co-pending application Ser. No. 829,645 of the present inventors that the measurement of density of, for example, bacteria suspended in a nutrient medium, can provide a reliable indicator of bacteria concentration. This invention can provide a test cell for use with advantage in the method according to that invention.

The importance of the length to thickness ratio of the tube has been stressed and the value of this ratio in the described embodiment quoted as 600. The ratio with advantage exceeds 150 and should be greater than 100. The tube may be folded in shapes other than a helical coil; a flat spiral or a planar serpentine arrangement suggest themselves. It is preferred that the tube is folded in such a way that the unfolded length of the tube is at least five times greater than the largest overall dimension of the coil or other folded arrangement.

The method of which the coil is excited at both ends with respective, out-of-phase signals has the advantage of increasing control over the vibratory movement enabling this to be brought closer to the ideal of simple harmonic motion of the tube as a whole. This may be regarded as a form of push-pull or differential drive and does not excite modes of torsional vibration. Unwanted torsional vibration of the tube can further be inhibited by means of a support—for example in the form of a sleeve—which holds the turns of the coiled tube in fixed relative position. Because the tube moves bodily, the resonant frequency is determined primarily be fluid density and viscosity effects are eliminated or significantly reduced. In certain circumstances, other drive arrangements might be employed.

The use of electrical coils and ferro-magnetic pole pieces for the drive means represents only one of the options available. It would be possible, for example, to use piezoelectric devices or—for the pick-up—a capacitative effect device. Alternatively, a small current may be passed through the stainless steel tube enabling this to serve as an electrical coil in cooperation with fixed coils or pole pieces. An embodiment of the invention exemplifying this modification will now be described.

Figure 5:
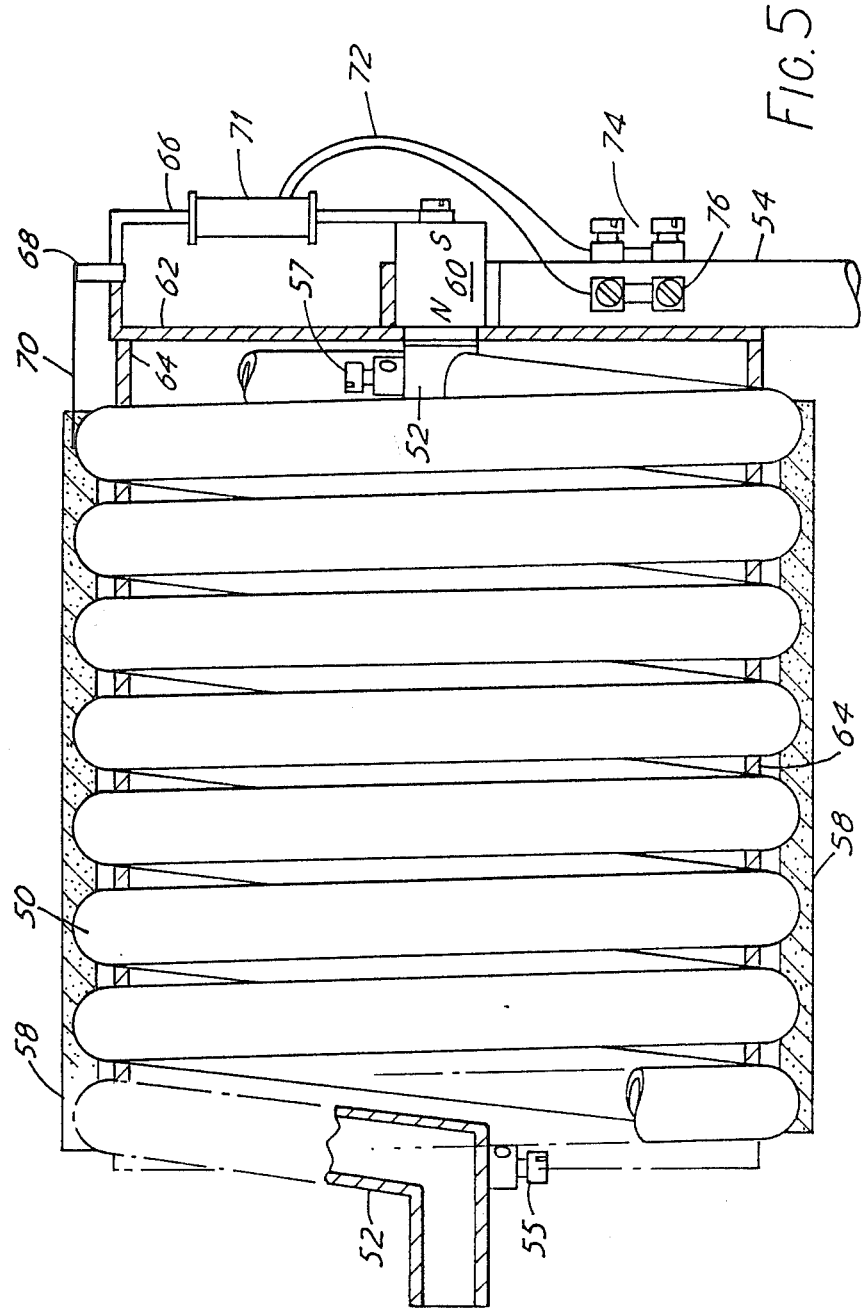
FIG. 5 is a side view showing apparatus according to a further aspect of the invention.
Figure 6:
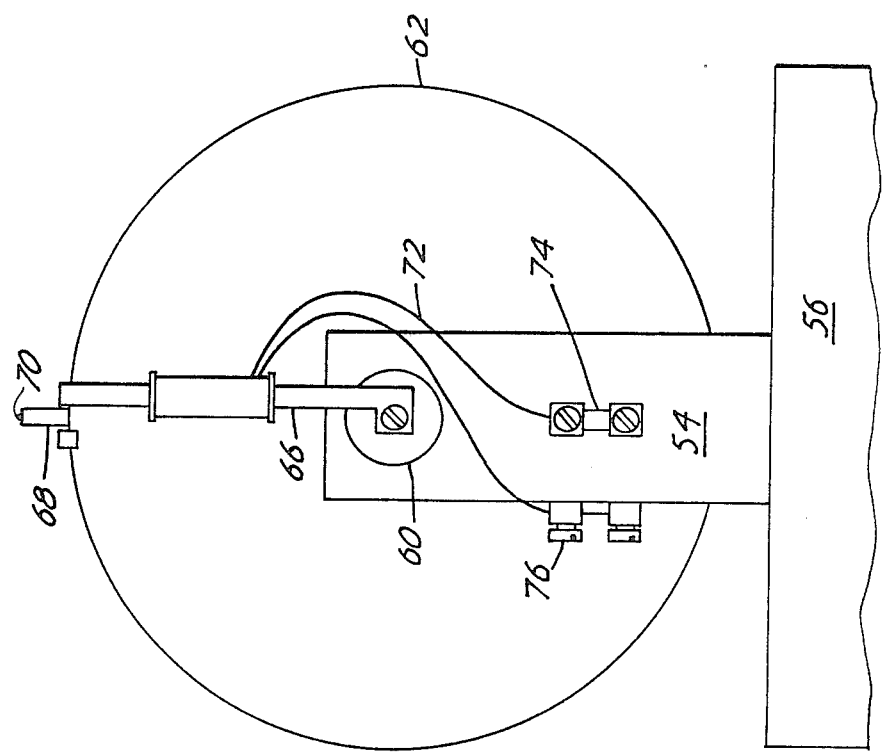
FIG. 6 is an end view of the apparatus shown in FIG. 5.

Referring now to FIG. 5, a helical sample tube 50 is formed for example of stainless steel. The ends of the tube are formed integrally with mounting portions 52 which are carried on respective posts 54 (only one seen in drawings) forming, with base plate 56, a rigid base structure. The mounting portions 52 also serve to define sample inlet and outlet ports together with the tube electrodes 55, 57. A coil fixing sleeve 58 of cylindrical form surrounds the helical sample tube 50 and firmly engages the helical turns of the tube to prevent relative movement of the turns. The sleeve is, in the preferred example, formed of a plastics material which undergoes slight shrinkage on the application of heat with the sleeve being positioned over the helical tube as a relatively loose fit and then heated to adopt the configuration shown in the drawing.

A high flux permanent magnet 60 is carried on one post 54 and is aligned along the axis of the sample tube. Inwardly of the post 54 the magnet is provided with a disc-shaped pole piece 62 carrying a hollow, cylindrical pole extension 64 which extends within the helical sample tube. The pole piece and extension are preferably formed of Formar.

A ferro-magnetic bridge piece 66 extends from the outward face of the magnet 60 to the top of the pole pice 62, this bridge carrying a reluctance stud 68 with a finger 70 extending axially over at least the first turn of the helical sample tube. A field coil 71 is mounted on the bridge 66 and is connected through leads 72 to field coil terminals 74, 76 on the post 54.

Figure 7:
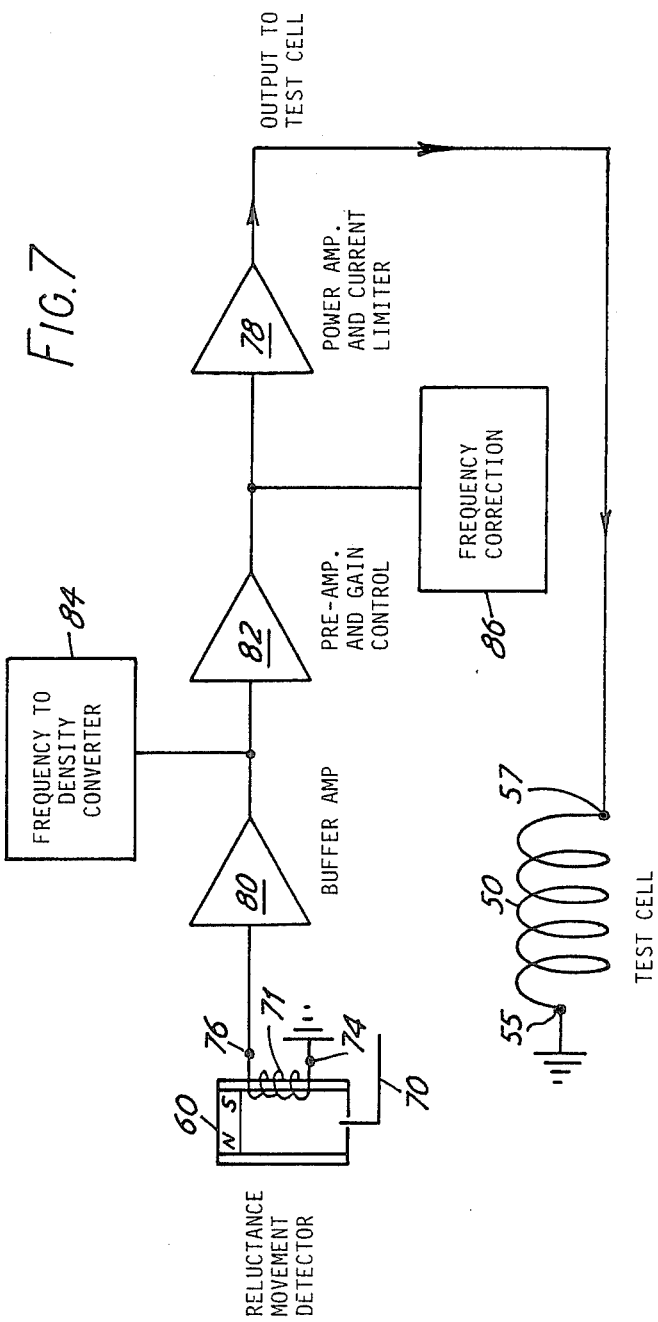
FIG. 7 is a circuit diagram showing the electrical drive for the apparatus shown in FIG. 5.

As shown in FIG. 7, one terminal 55 of the helical sample tube is connected to earth, the other terminal 57 being connected to the output of a high gain operational amplifier 78. The field coil terminals 74, 76 are connected one to earth and the other to the input of the amplifier 78 through buffer 80 and pre-amp 82. In analogous manner to the embodiment described above, any slight movement of the sample tube relative to the base will—through a change in reluctance—result in a current flow in field coil 70. Through the amplifier stages 78, 80, 82 an excitation current is thus applied to the sample tube. Having regard to the magnetic field established by magnet 60 and the pole extension 64, each current-carrying length element of the sample tube will be subjected to an axial force, the sum of these forces resulting in bodily axial movement of the sample tube. It will be understood that the current in the field coil 70 is thus modulated with the resulting feedback to the amplifier tending to drive the sample tube into resonance. A frequency meter 84 is provided to measure the resonant frequency, and a frequency correction device 86 may be provided if required.

Since each turn of the helical tube receives a like displacement force, torsional modes of vibration are not excited. The sleeve 58 further serves to prevent torsional movement and ensures that vibration is confined to the translational mode. Accordingly, a resonant frequency is established which is indicative of the density of the fluid and which is not dependent (or which is dependent to an insignificant degree) upon the viscosity of the fluid.

Figure 8:
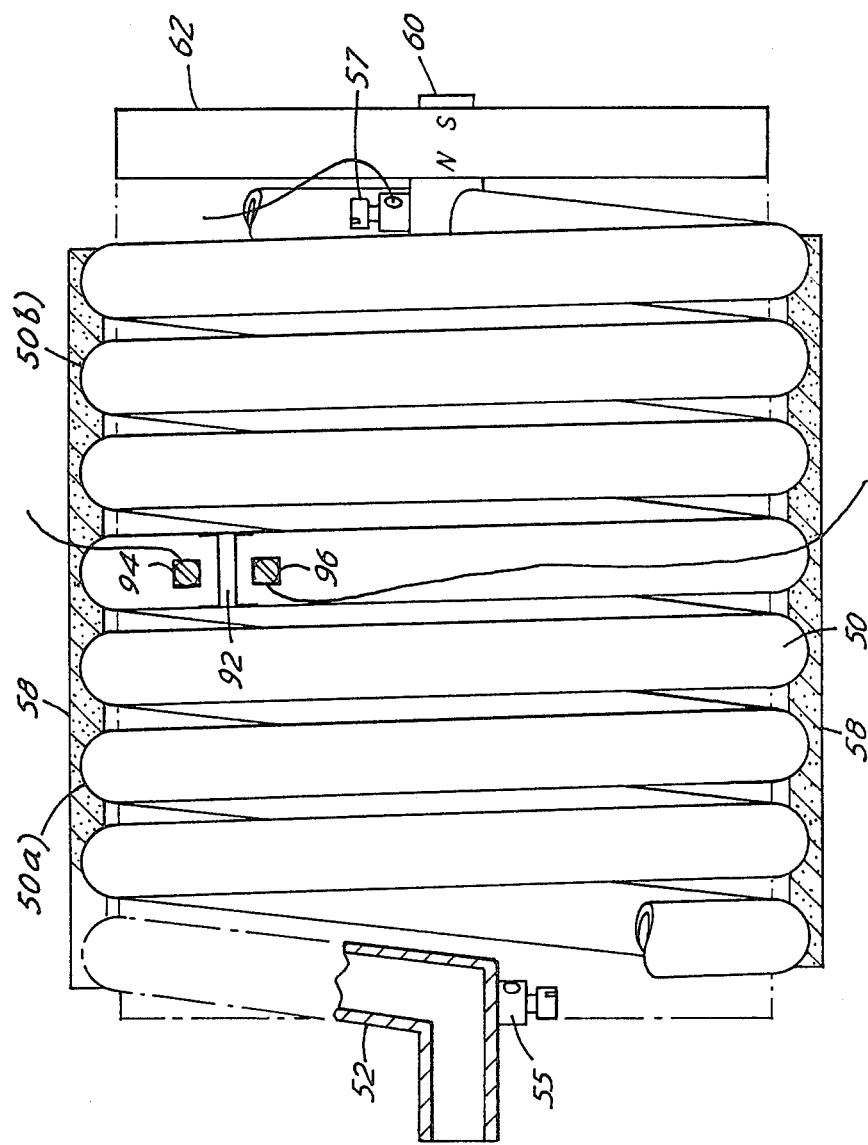
FIG. 8 is a view similar to FIG. 5 illustrating a modification.

A modification to this invention is illustrated in FIG. 8. Elements which are common to the embodiment of FIG. 5 retain the same reference numerals and will not be described in detail. The helical sample tube 50 is divided into first and second axial portions 50a) and 50b) which are then connected through a PTFE or other electrically insulating connector piece 92. Terminals 94 and 96 are provided on the respective coil portions immediately adjacent the connector piece 92.

Figure 9:
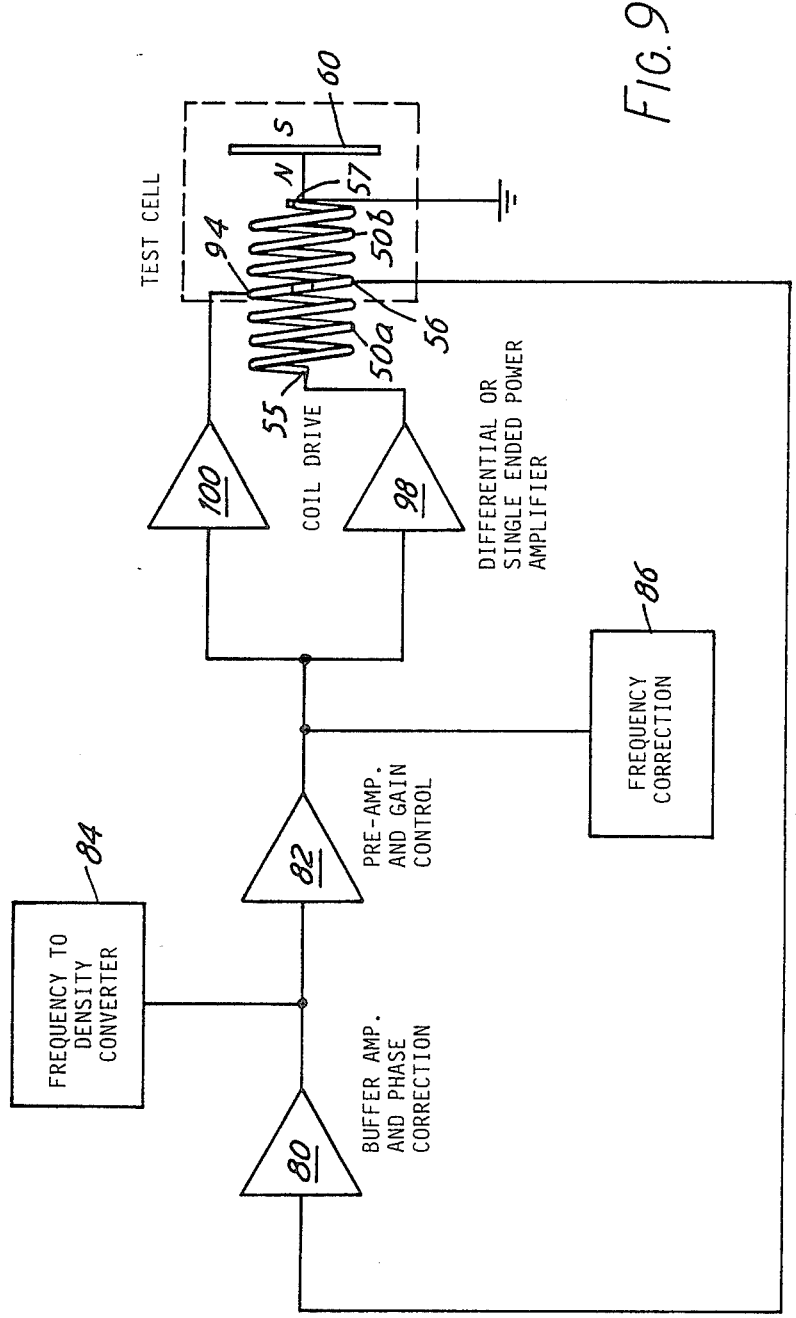
FIG. 9 is a circuit diagram showing an electrical drive from the apparatus shown in FIG. 8.

As shown in FIG. 9, terminals 55 and 94 are connected to the outputs of respective amplifiers 98 and 100, this differential amplifier arrangement taking the place of single amplifier 78 in the circuit of FIG. 7. Terminal 57 is connected to earth whilst terminal 96 is connected to the inputs of amplifier 98, and 100 through common buffer and pre-amp stages 80 and 82.

Buffer 80 also serves to ensure that the feedback signal is applied in the correct phase.

As with the previous arrangement, the tube is excited into vibrational resonance and the resonant frequency determined. It should be understood that the division of the sample tube into two equal halves is shown by way of example only and the "drive" and the "field" elements of the helical tube could occupy different proportions of the total tube.

The ingenious manner in which the sample tube is made part of the drive system by the passage of an electrical current along the length of the tube has the obvious advantage of mechanical simplicity but has the more important functional advantage that each discrete length element of the tube can be arranged to receive the identical displacement force. as will be apparent from the embodiment described with reference to FIG. 8, the electrical current need not pass along the entire length of the tube although it is regarded as important that a substantial length of the tube should be used. In the simplest form, the entire tube is formed of electrically conductive material such as stainless steel. If necessary, however, an insulating tube lining of, for example, PTFE could be employed, it merely being necessary that there is a continuous portion of electrically conductive tube wall that extends over a substantial length of the sample tube.

In the described embodiment the current-carrying tube is positioned in the magnetic field created by a permanent magnet. It will be recognized by the skilled man that magnetic coupling of a fixed reactor with the current-carrying tube could be achieved in other ways, such as by the use of a fixed electromagnet. Indeed, in certain arrangements the reactor itself need not be magnetic and may form a fixed pole piece for the solenoid formed by the current-carrying tube. Still further alternatives will suggest themselves to the skilled man.

In a further modification, vibration of the sample tube may be monitored optically rather than electrically via the drive circuitry. In its simplest form such an optical monitor might take the form of a beam repeatedly broken on movement of the sample tube.

We claim:
1. Apparatus for use in measuring fluid density comprising:
   (A) a substantially rigid base structure;
   (B) a helical sample tube having a tube wall which is electrically conductive at least in a continuous portion thereof extending throughout a substantial length of the sample tube, the sample tube being fixed at end portions thereof on said base structure;
   (C) sample feed means for introducing into said sample tube a body of fluid whose density is to be measured;
   (D) drive means for the sample tube, comprising current means for passing an electrical current through said length of the sample tube and reactor means mounted on the base structure and adapted through magnetic coupling with the current carrying sample tube to excite bodily vibrational movement of the sample tube along the helical axis thereof; and
   (E) monitoring means for monitoring said vibrational movement to determine the fluid density.
2. Apparatus according to claim 1, further comprising feedback means connected between said monitoring means and said current means such that said drive means operates to excite the sample tube into vibrational resonance.
3. Apparatus according to claim 1, wherein said reactor means comprises a permanent magnet.
4. Apparatus according to claim 1, wherein said monitoring means includes a further continuous, electrically conductive tube wall portion extending throughout a substantial length of the sample tube electrically isolated from said length and magnetically coupled in like manner with said reactor means.
5. Apparatus for use in measuring fluid density comprising:
   (A) a substantially rigid base structure;

(B) a helical sample tube having a tube wall which is electrically conductive at least in a continuous portion thereof extending throughout a substantial length of the sample tube, the sample tube being fixed at end portions thereof on said base structure;

(C) sample feed means for introducing into said sample tube a body of fluid whose density is to be measured;

(D) drive means for the sample tube, comprising current means for passing an electrical current along said length of the sample tube and reactor means mounted on the base structure and adapted through magnetic coupling with the current carrying sample tube to excite bodily vibrational movement of the sample tube along the helical axis thereof; and (E) monitoring means for monitoring said vibrational movement to determine the fluid density, wherein support means are provided on the sample tube to prevent relative movement of the helical turns of the sample tube.

6. Apparatus according to claim 5, wherein said support means comprises a cylindrical sleeve surrounding the helical sample tube and engaging the sample tube wall.

7. Apparatus for use in measuring fluid density, comprising a thin, elongate tube fixed only at its ends and folded between said ends; support means for preventing torsional movement of the folded tube; a pair of electro-mechanical drive means operating on the tube at spaced locations adjacent respective opposite ends of the tube, said electro-mechanical drive means being supplied with out of phase electrical signals to excite bodily vibrational movement of the tube and monitoring means including a transducer operating near the mid-length of the tube for monitoring the vibratory movement of the tube to determine fluid density.

8. Apparatus according to claim 7, wherein each said electromechanical drive means comprises a solenoid cooperating with a pole piece mounted on the corresponding end of the tube.

9. Apparatus according to claim 7, wherein the tube is folded in a helical coil.

10. Apparatus according to claim 7, wherein the ratio of the unfolded length of the tube to the thickness of the tube is equal to or greater than 100.

11. Apparatus according to claim 10, wherein said ratio is around 600.

12. Apparatus according to claim 7, wherein the tube is folded in a helical coil and said support means comprises a cylindrical sleeve surrounding said coil.

13. Apparatus for use in measuring fluid density, comprising an element adapted to contain a body of fluid and mounted for vibratory movement; means for driving the element and means for monitoring said vibrational movement to determine the fluid density wherein the element comprises a thin, elongate tube fixed only at its ends and folded between said ends, in which the ratio of the unfolded length of the tube to the thickness of the tube is equal to or greater than 100, there being provided support means adapted to prevent torsional movement of the folded tube.

14. Apparatus according to claim 13, wherein said ratio is equal to or greater than 600.

15. Apparatus according to claim 13, wherein said means for driving the vibratory element comprises a pair of electro-mechanical drive means operating on the element at spaced locations and supplied with out of phase electrical signals.

16. Apparatus according to claim 15, wherein the electro-mechanical drive means comprise respective solenoids cooperating with corresponding pole pieces mounted at opposite ends of the tube.

17. Apparatus according to claim 13, wherein said tube is formed of metal and said means for driving the element comprises means for passing a current along a substantial portion of the length of the tube and a reactor magnetically coupled with the current carrying tube portion.

18. Apparatus for use in measuring fluid density, comprising a sample element mounted for translational vibratory movement and defining an internal tortuous sample cavity having a thickness and a length which is at least one hundred times greater than said thickness; means for driving the element and means for monitoring said vibrational movement of the element to determine the fluid density, wherein said sample element comprises a helical coil with said support means adapted to prevent relative movement between helical turns of the coil.

* * * * *